June 6, 1944. B. D. DRAIN Plant Pat. 629

STRAWBERRY PLANT

Filed Dec. 15, 1942

Inventor
Brooks D. Drain
By Cameron, Kerkam & Sutton Attorneys

Patented June 6, 1944

Plant Pat. 629

UNITED STATES PATENT OFFICE

629

STRAWBERRY PLANT

Brooks D. Drain, Knoxville, Tenn., assignor to The University of Tennessee Research Corporation, Knoxville, Tenn., a corporation of Tennessee Application December 15, 1942, Serial No. 469,092

1 Claim. (Cl. 47—62)

This invention pertains to the asexual reproduction of strawberry plants, and specifically to the asexual reproduction of a new and distinct variety of strawberry produced by the artificial pollination of the Missionary plant with pollen from the Howard (Premier) strawberry.

The object of the invention is to produce a novel variety of strawberry plant which possesses better commercial qualities than varieties now in existence ripening in mid-season to late and which is particularly adapted to the soil and climate of the State of Tennessee.

The new variety produces large crops of large attractive berries; larger yields and better quality fruit than Aroma which ripens at the same season. Comparable plots in various parts of Tennessee have averaged larger yields than Blakemore, a variety extensively grown in that State for the early market. It is free from the "yellow leaf" trouble which is so destructive among Blakemore plants.

In the accompanying drawing.

Figure 1:
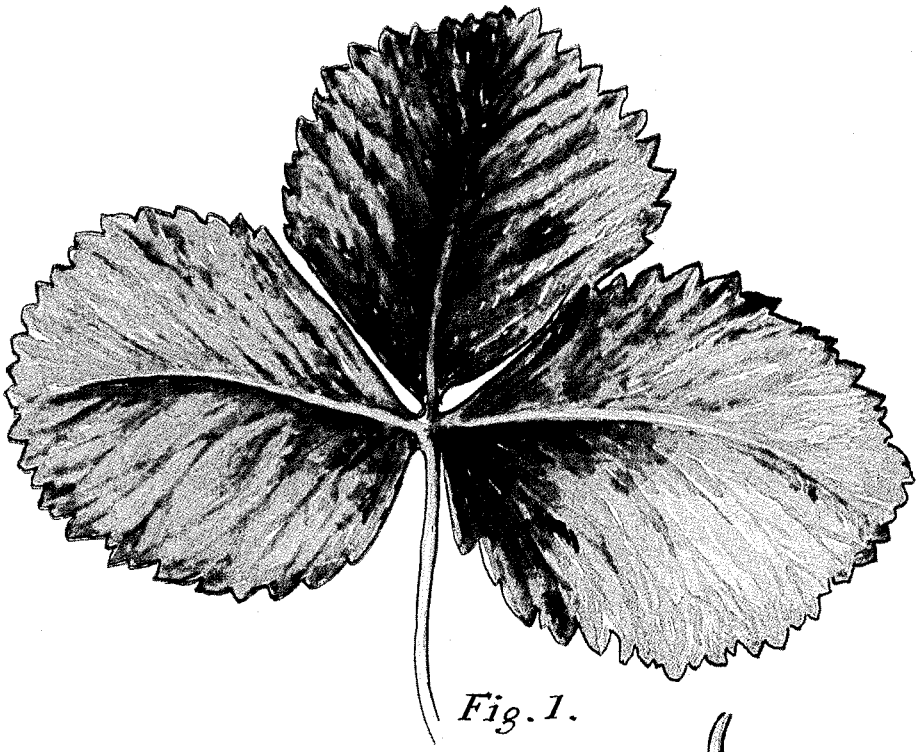
Fig. 1 is a view of a leaf of the plant showing its color and other characteristics.
Figure 2:
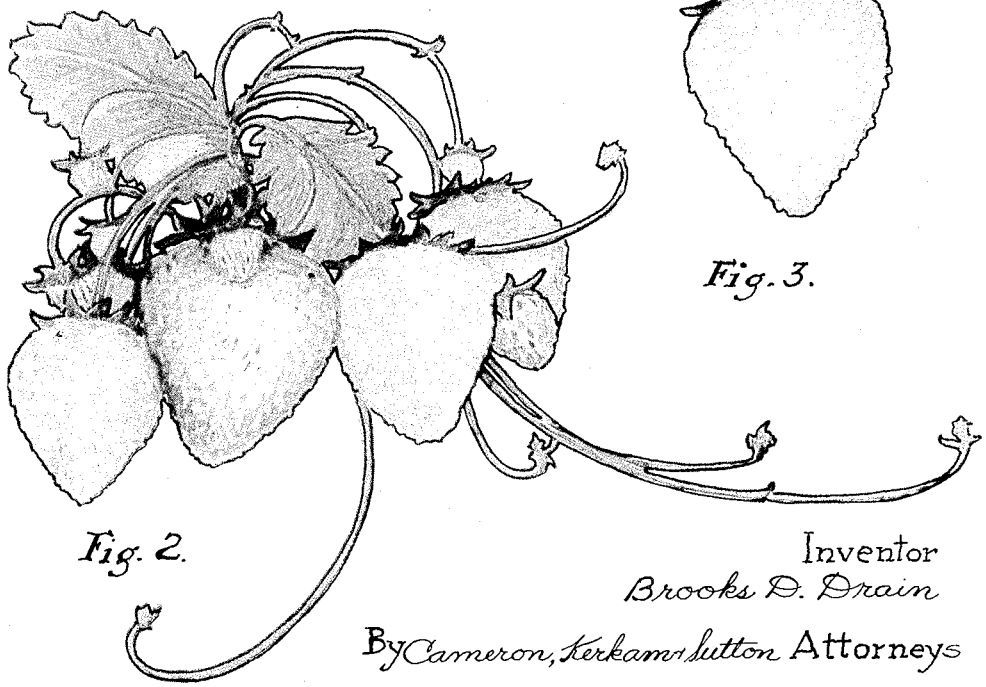
Fig. 2 is a longitudinal section of a berry of the new plant showing its internal color and characteristics.
Figure 3:
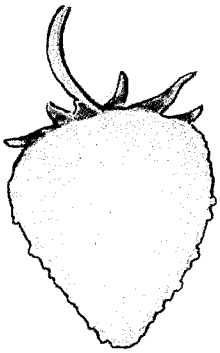
Fig. 3 is a view of a fruiting stem of the plant showing ripe and green berries.

In producing the plant of the present invention, the pollen of the Howard (Premier) strawberry was placed in the blossom of Missionary plants, the pollen producing parts of the blossoms of the Missionary having first been removed. The pollinated blossoms were then protected so that they could not receive pollen from any other plant, and were allowed to develop into fruit. The seeds from this fruit were then planted and permitted to sprout, and after the plants had grown to sufficient size, they were transplanted and allowed to fruit in the field. At about the time the plants were fruiting in the field each plant and its vegetatively developed runner plants were examined for freedom from insects and diseases and for desirable growth habits. The fruit was also tested and examined for desirable fruit characteristics. The best among a large number of seedlings was then selected and saved and propagated asexually, using runner plants to produce the plant of the present invention. All of the plants which are now growing, including the one from which the accompanying drawing was made, have come from this original seedling.

The new variety differs from its parent varieties in numerous respects. The fruit ripens later than that of either parent and the yield is larger under Tennessee conditions. The plants are darker green in color and stockier than Missionary. Under Tennessee conditions more runner plants are formed from a given number of mother plants of the new variety than with Howard (Premier). Compared with the Missionary the fruit of the new variety is larger, darker red in color, and better flavored. The berries of the Howard (Premier) are softer than those of the new variety.

One vigorous mother plant of the new variety will produce from a few to more than one hundred runner plants, depending upon soil fertility and growing conditions, and large crops of medium red berries will be produced in mid-season to late. The foliage of the plant is medium in size, medium green in color, smooth and glossy. Some leaf blight and leaf spot have been noted, but the foliage is comparatively healthy.

The berries produced by this plant are large in size and retain their size throughout the season. Their shape varies from long conic to round conic with a few berries wedge-shaped. The surface of the berry is medium red in color, glossy and attractive. The flesh is firm, medium red and somewhat lighter colored toward the center. The fruit is subacid and good in flavor. Other characteristics of the new strawberry are as follows:

Plants: Medium in number; vigorous; medium in height; very productive; spring bearing.

Susceptibility:

*Insect.*—Weevil.

*Diseases.*—Some blight and leaf spot.

Runners: Medium in length; medium in thickness; internodes medium.

Leaves: Medium in size; medium green in color; smooth; glossy.

Petiole: Medium in thickness.

Flowers: Perfect.

*Date of bloom.*—April 12, 1941, at Jackson, Tennessee. Medium in time of bloom.

*Length of blooming season.*—1 month.

Size: Diameter, 1⅛ inches. Medium in size.

Petals: Number, 5 to 7. Large in size.

Stamens: Numerous.

Receptacle: Medium in size.

Fruit stems: Long; medium in thickness; semi-erect.

Pedicels: Medium in length; medium thickness.

Fruit:

*Season.*—Midseason to late.

*Date of ripening.*—Started May 13, 1941, at Jackson, Tenn.

*Length of season.*—Two to three weeks.

Picking quality: Good (long stems).

Shipping quality: Good. Large in size; retains size; uniformity good; regular; round conic to long conic, sometimes wedged.

Apex: Pointed.

Surface color: Medium Red R4/8 (Munsell Book of Color, published by Munsell Color Co., Inc., 1929). Glossy; attractive; colors evenly.

Calyx: Large; raised; leafy.

*Color.*—Medium green.

*Adherence to Fruit.*—Medium.

Sepals: Long; medium in width.

Seeds: Medium in number. Sunken, rarely raised.

Flesh: Medium Red in color R5/12 (Munsell Book of Color); slightly lighter towards the center. Juicy; firm; subacid.

Quality: Good.

Use: Dessert; canning; market; home.

Desirability: A good late ripening variety.

What is claimed is:

A healthy, prolific strawberry plant variety substantially as illustrated and described, characterized by subacid, well flavored fruits which are medium red becoming lighter toward the center of the berry, which ripen from midseason to late, and by the development of a large number of runner plants.

BROOKS D. DRAIN.